United States Patent [19]

Wilcox et al.

[11] Patent Number: 5,232,695
[45] Date of Patent: Aug. 3, 1993

[54] METHOD OF AMELIORATING HERPES SIMPLEX VIRUS INFECTIONS USING PURIFIED NERVE GROWTH FACTOR

[75] Inventors: Christine L. Wilcox, Denver, Colo.; Eugene M. Johnson, Jr., St. Louis, Mo.

[73] Assignee: G. D. Searle & Co., Chicago, Ill.

[21] Appl. No.: 624,488

[22] Filed: Dec. 6, 1990

Related U.S. Application Data

[63] Continuation of Ser. No. 137,274, Dec. 23, 1987, abandoned.

[51] Int. Cl.$^5$ .................... A61K 37/02; A61K 39/12
[52] U.S. Cl. .......................... 424/89; 514/2; 514/12; 514/21; 514/931; 514/934
[58] Field of Search ............... 424/89; 514/2, 12, 21, 514/934, 931

[56] References Cited

U.S. PATENT DOCUMENTS 4,341,762  7/1982  Haast ........................ 424/88
4,760,079  7/1988  Baldone ..................... 514/642

OTHER PUBLICATIONS

E. M. Johnson, Jr. et al, *Nature (London)*, 314, 751-752 (1985).
I. A. Hendry et al, *Brain Res.*, 68, 103-121 (1974).
H. Thoenen et al, *Physiol. Rev.*, 60, 1284-1335 (1980).
R. W. Price et al, *Infect. Immun.*, 19, 523-532 (1978).
W. A. Blyth et al, *J. Gen. Virol.*, 33, 547-550 (1976).
S. L. Warren et al, *J. Exp. Med.*, 71, 155-168 (1940).
C. A. Carton et al, *N. Engl. J. Med.*, 246, 172-176 (1952).
M. A. Walz et al, *Science*, 184, 1185-1187 (1974).
L. I. Pizer et al, *Acta. Neuropathol. (Berl.)*, 44, 9-14 (1978).
B. L. Wigdahl et al, *Virology*, 127, 159-167 (1983).

*Primary Examiner*—F. T. Moezie
*Attorney, Agent, or Firm*—Roberta L. Hastreiter; Paul D. Matukaitis

[57] ABSTRACT

Methods of treatment are described for use of purified nerve growth factor to ameliorate viral infections in an animal caused by Herpes Simplex Virus Types 1 and 2. Compositions are described for use in the treatment comprising purified nerve growth factor alone or in conjunction with a Herpes Simplex Viral antiviral agent.

10 Claims, 1 Drawing Sheet

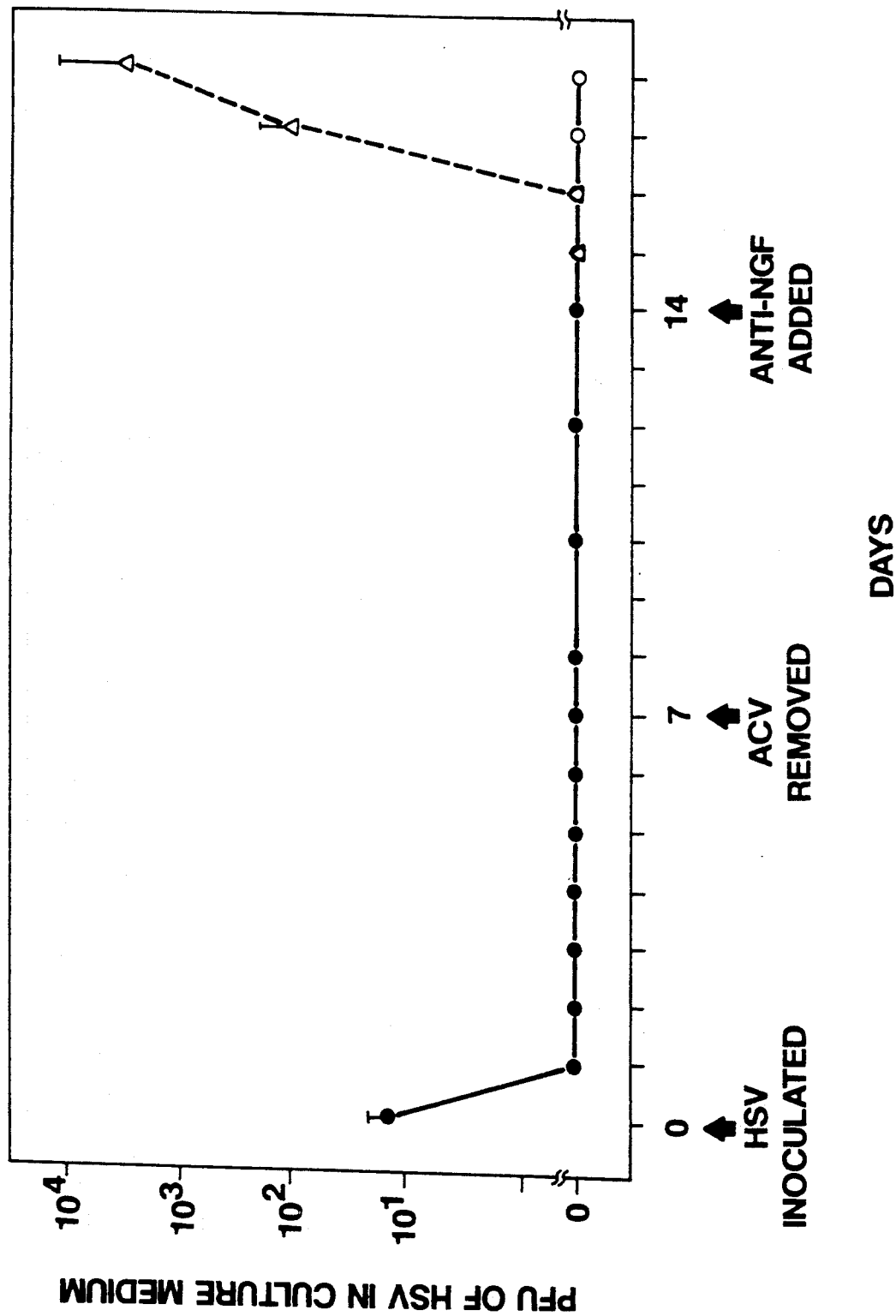

METHOD OF AMELIORATING HERPES SIMPLEX VIRUS INFECTIONS USING PURIFIED NERVE GROWTH FACTOR

This is a continuation of U.S. patent application Ser. No. 07/137,274, filed Dec. 23, 1987, now abandoned.

FIELD OF THE INVENTION

This invention is in the field of neurovirology and relates to methods of ameliorating viral infections. Of particular interest are methods for treating neurons infected with herpes simplex virus and in regulating the latent state of the virus within infected neurons.

BACKGROUND OF THE INVENTION

Herpes simplex virus (HSV) causes diseases in humans which range in severity from the benign cold sore to life-threatening encephalitis. Herpes simplex virus (HSV) resides in a latent state in neurons of sensory and sympathetic ganglia. During latency, infectious virus is not detectable; however, the latent virus can reactivate to produce recurrent lesions and transmissible virus. The mechanisms involved in the establishment, maintenance and reactivation of latent HSV are not understood.

It is known that nerve growth factor (NGF) endogenous to the central nervous system (CNS) and peripheral nervous system (PNS) provides trophic support critical to mature sensory neuronal survival [E. M. Johnson, Jr. et al., *Nature* (London), 314, 751–752 (1985)]. Nerve growth factor is synthesized and released by peripheral target tissue. NGF binds specifically to receptors on the nerve terminals and is retrogradely transported to the neuronal soma [I. A. Hendry et al., *Brain Res.*, 68, 103–121 (1974)]. Sympathetic and neural crest-derived sensory neurons in vivo and in vitro require NGF for maintaining normal function and, depending on age and cell type, for survival [H. Thoenen et al., *Physiol. Rev.* 60, 1284–1335 (1980)].

The HSV genome resides within neuronal cells during latency. Reactivation of latent HSV has been attributed to a number of diverse causes. For example, the loss of trophic support provided to the neuron by the peripheral target has been suggested to result in reactivation of latent HSV [R. W. Price et al., *Infect. Immun.*, 19, 523–532 (1978)]. Examples of other reactivating stimuli are UV irradiation and fever [W. A. Blyth et al., *J. Gen. Virol.*, 33, 547–550 (1976); and S. L. Warren et al., *J. Exp. Med.*, 71, 155–168 (1940)]. Still other reactivating stimuli may act by reducing or interrupting retrogradely transported neurotrophic support from neuronal targets, such as by central rhizotomy or axotomy [C. A. Carton et al., *N. Engl. J. Med.* 246, 172–176 (1952); M. A. Walz et al., *Science,* 184, 1185–1187 (1974)].

Others have investigated HSV latency, reactivation and replication. For example, cells of neural crest origin (PC-12, pheochromocytoma cell line) cultured in the presence of NGF can be infected with herpes simplex virus and produce progeny virus [L. I. Pizer et al., *Acta. Neuropathol.* (Berl.), 44, 9–14 (1978)]. Establishment and maintenance of latency of HSV-infected neuronal cells have been accomplished using complicated combinations of chemical agents, physical conditions and biological reagents. For example, one HSV latency model requires (i) BVDU and IFN-α to establish latency, (ii) elevated temperature to maintain latency, and (iii) temperature reduction along with human cytomegalovirus super-infection to reactivate the virus [B. L. Wigdahl et al., *Virology,* 127, 159–167 (1983)].

Aside from those attempts to establish models to investigate the in vivo interactions of HSV with neuronal cells, present therapeutic approaches to treatment of animals infected with active HSV usually depend upon the administration of drugs as anti-viral agents. Many of these anti-viral agents are minimally effective, however, or must be utilized at sub-optimal concentrations because of severe side effects of the anti-viral agent on the animal. Hence, a need exists for an agent which can ameliorate viral disease while having little detrimental effect on host tissues.

SUMMARY OF THE INVENTION

A reduction in HSV infectious activity or maintenance of HSV in a latent state in an animal can be accomplished by methods which comprise administering to the animal a therapeutically effective amount of nerve growth factor (NGF). These methods may also include administering NGF in combination with one or more anti-viral agents.

A benefit provided by this treatment method is the absence of significant detrimental side effect by use of NGF, inasmuch as NGF is a naturally-occuring, endogenous substance which is found in animal neuronal tissue.

As another benefit, NGF may be used in combination with one or more anti-viral agents such as, for example, acyclovir, with therapeutic effects obtained at lower concentrations of the anti-viral agent than would be possible if NGF were not co-administered. Thus, the risk of detrimental side-effects due to the anti-viral agent can be reduced. In addition, combination treatments of two anti-viral agents, such as NGF and acyclovir, may decrease the emergence of strains resistant to either anti-viral agent.

BRIEF DESCRIPTION OF THE FIGURE

FIG. 1 shows the expression of infectious virus during the establishment of latent infections and during the reactivation of HSV after NGF deprivation from neuronal cultures inoculated with HSV in the presence of acyclovir (ACV). The ACV was removed after seven days. When NGF deprivation was subsequently produced by the addition of 1% anti-NGF serum to the neuronal cultures (Δ), virus was detected in the culture supernatants from 100% of the cultures 72 hours after the addition of anti-NGF. Neuronal cultures treated with 1% nonimmune serum () did not produce detectable virus. Results are expressed as the mean of the number of plaque-forming units (PFU) recovered in the media from four cultures per time point (±SEM).

DETAILED DESCRIPTION

NGF is effective in preventing HSV primary infection and in suppressing active HSV, as well as in preventing reactivation of latent viral infections.

Purified NGF is known [Cohen, *Proc. Nat'l Acad. Sci.* (USA), 46, 302 (1960). While desirable, it is not essential that the NGF be derived from the same species for which it is to be used in the treatment methods of this invention. Nerve growth factor may be administered for therapy by any suitable route including oral, rectal, nasal, topical (including buccal and sublingual), vaginal and parenteral (including subcutaneous, intramuscular, intravenous and intradermal). The preferred route may vary, for example, with the condition and age of the recipient and the nature and the location of the infection.

The term "HSV" is a short-hand term intended to embrace Herpes Simplex Virus type 1 (HSV-1) and Herpes Simplex Virus type 2 (HSV-2). The term "ameliorate" denotes a lessening of the detrimental effect on an animal due to the HSV infection. For example, the method of NGF treatment may lessen the likelihood that a primary viral infection will occur, or may suppress the action of active HSV, or may lessen the likelihood that a latent viral infection will become reactivated. The term "therapeutically effective" amount means that amount of nerve growth factor which is capable of ameliorating HSV detrimental effects. The term "animal" embraces both humans and non-humans.

In general, a suitable daily dose of NGF will be that amount of NGF which is the lowest dose effective to produce a therapeutic effect. Such an effective dose generally will depend upon the weight of the recipient. The dose may be in a range from about 0.01 mg to about 10 mg per kilogram body weight per day, or in a range from about 0.01 mg to about 5 mg per kilogram body weight, or in a range from about 0.01 to about 2.5 mg per kilogram body weight per day. The desired dose can be presented as two, three, four, five, six or more sub-doses administered at appropriate intervals throughout the day. These sub-doses may be administered in unit dosage forms.

While it is possible for NGF to be administered alone, it is preferable to administer NGF as a pharmaceutical formulation. The formulations of the present invention comprise NGF together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including buccal and sublingual), vaginal or parenteral (including subcutaneous, intramuscular, intravenous and intradermal administration. The formulations may conveniently be presented in unit dosage form and may be prepared by any methods well known in the art of pharmacy. Such methods include the step of bringing into association NGF with the carrier which constitutes one or more accessory ingredients. In general, the formulations are prepared by uniformly and intimately bringing into association NGF with liquid carriers, or finely divided solid carriers, or both, and then if necessary shaping the product.

Formulations of NGF suitable for oral administration may be in the form of capsules, cachets or tablets, each containing a predetermined amount of NGF, or as a powder of granules, or as a solution or a suspension in an aqueous or non-aqueous liquid, or as an oil-in-water liquid emulsion, or a water-in-oil liquid emulsion. NGF may also be administered as a bolus, electuary or paste.

A tablet may be made by compression or molding, optionally with one or more accessory ingredients. Compressed tablets may be prepared by containing NGF mixed with binder (for example, gelatin or hydroxypropylmethyl cellulose), lubricant, inert diluent, preservative, disintegrant (for example, sodium starch glycollate or cross-linked sodium carboxymethyl cellulose), surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may be provided with an enteric coating, to provide release in parts of the body other than the stomach.

Formulations suitable for oral administration include lozenges comprising NGF in a flavored basis, usually sucrose and acacia or tragacanth; pastilles comprising NGF in an inert basis such as gelatin and glycerin, or sucrose and acacia; and mouth washes comprising NGF in a suitable liquid carrier.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to NGF such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

NGF may also be used in the form of veterinary formulations, including those adapted for:

(a) oral administration, for example, drenches (aqueous or non-aqueous solutions or suspension); tablets or boluses; powders, granules or pellets for admixture with feed stuffs; pastes for application to the tongue;

(b) parenteral administration, for example, by subcutaneous, intramuscular or intravenous injection as for example, a sterile solution or suspension; or, when appropriate, by intramammary injection where a suspension or solution is introduced into the udder via the teat;

(c) topical application, for example, as a cream, ointment or spray applied to the skin; or (d) intravaginally, for example, as a pessary, cream or foam.

NGF may also be used in therapy in conjunction with antiviral agents. One preferred group of antiviral agents consist of those which inhibit viral DNA polymerase. Such agents are known and include, for example, acyclovir and phosphonoacetic acid.

EXAMPLE 1

GENERAL TECHNIQUES

A. Preparation of viruses.

HSV-1 (115), a recent clinical isolate obtained from Dr. Charles Reed (St. Louis Children's Hospital, Virology Laboratory, St. Louis, Mo.) was used unless otherwise indicated. HSV-1 (F), HSV-1 (McIntyre), HSV-2 (G) and Vero cells were purchased from American Type Culture Collection (Rockville, Md.). HSV-1 (KOS) and HSV-1 (HRM) were provided by L. I. Pizer (University of Colorado Health Sciences Center, Denver, Colo.). HSV-1 (HRM) is a host range mutant prepared by Berge Hampar by passage of wild type strain 14–120 in the presence of bromodeoxyuridine. Viruses were grown and quantitated by plaque assay on confluent Vero cells.

B. Neuronal cultures.

Sympathetic neuronal cultures were prepared from superior cervical ganglia from prenatal rats (Zivic-Miller Laboratories, Inc., Zelienople, Penn.) essentially as described by Johnson, et al. (*Methods in Enzymology*, 103, 334,1983). Briefly, the ganglia were removed aseptically and incubated for 1 h at 37° C. with 1 mg/ml collagenase (Cooper Biomedical, Inc., West Chester, Penn.). After rinsing with medium, the ganglia were mechanically dissociated and plated onto 15-mm, 4-well culture dishes (Nunc, Roskilde, Denmark) coated with rat-tail collagen at a density of 5000–8000 neurons per culture. The cultures were maintained with Eagle's minimal essential medium (GIBCO Laboratories, Grand Island, N.Y.) supplemented with 1.4 mM glutamine (Sigma, St. Louis, Mo.), 10% fetal calf serum (GIBCO Laboratories) and 50 ng/ml 2.5S mouse NGF, prepared by the method of Bocchini, et al. (*Proceedings of the National Academy of Sciences, U.S.A.*, 64, 787, 969), and incubated at 36° C. in an atmosphere of 5% $CO_2$. The culture medium was renewed every 3–5 days. For the first 10–12 days after plating, the cultures were treated with 20 uM fluorodeoxyuridine (Sigma) which reduced the nonneuronal cell population to less than 5%, but did not effect the neurons.

C. Establishment and reactivation of latent HSV.

Unless noted otherwise, ten to twelve days after plating, acyclovir (ACV) (Burroughs Wellcome Co., Research Triangle, N.C.), aphidicolin (Calbiochem, La Jolla, Calif.), or phosphonoacetic acid (Sigma) was added, at the concentrations indicated in the table and figure legends, to the cultures 12 h prior to inoculation with HSV. The multiplicity of infection (MOI) with HSV used is indicated in the table and figure legends. Seven days after inoculation, the drug treatment was discontinued by washing with several changes of the standard medium. Cultures were tested, by using the culture supernatants in plaque-forming assays, for the presence of infectious virus at various times following inoculation. Fourteen days or longer after inoculation with virus, the cultures were evaluated for the presence of latent HSV. To reactivate latent virus, cultures were deprived of NGF by adding to the culture medium 1% heat-inactivated, anti-NGF serum. The anti-NGF serum had a titer of 32,000, defined as the reciprocal of the highest dilution preventing neurite outgrowth in the standard embryonic chick dorsal root ganglia bioassay (Fenton, *Experimental Cell Research*, 59, 383, 1970). Neutralizing antibodies to NGF were obtained by immunizing guinea pigs with mouse NGF in complete Freund's adjuvant (Rich, et al., *Journal of Comparative Neurology*, 230:110,1984). Latent cultures were treated with 1% heat-inactivated, nonimmune guinea pig serum as a control.

D. Immunohistochemistry.

Cultures were grown as described on collagen-coated coverslips (Miles Laboratories, Naperville, Ill.). Cultures were fixed with 4% paraformaldehyde in phosphate-buffered saline (PBS) for 10 min. The coverslips were dried and mounted onto microscope slides. The slides were processed for indirect immunohistochemistry using the avidin-biotin-enzyme complex method (Vectastain, Vector Laboratories, Burlingame, Calif.). The cells were permeabilized by treatment with 0.5% NP-40 (Sigma) for 10 min. Two primary antibodies were used. A polyclonal human anti-HSV-1) was diluted 1:200 in PBS containing 1% bovine serum albumin, fraction V (Sigma). Anti-IGP4, a monotypic rabbit antiserum prepared against the immediate early gene ICP4 which is overproduced by the mutant HSV-1 (tsK) at the nonpermissive temperature, was diluted 1:50 in PBS+1% bovine serum albumin, fraction V. The primary antibodies were incubated with the slides overnight at 4° C. The slides were washed three times with cold PBS and then incubated at room temperature for 1 h with the biotinylated antibody diluted 1:200 in PBS. The cultures were rinsed and incubated at room temperature with the avidin-biotin-glucose oxidase complex (Vector Laboratories) for 30 min. For the final reaction product, the slides were incubated with nitroblue tetrazolium (Substrate Kit I, Vector Laboratories) for 30 min. at 37° C., and rinsed with distilled water; coverslips were mounted with glycerol-PBS.

EXAMPLE 2

INHIBITION OF VIRAL REACTIVATION AT VARIOUS LEVELS OF MOI

Neuronal cultures were treated with ACV from 2 h prior to and for 7 days after inoculation with HSV; thereafter, ACV was removed. ACV had no apparent toxic effects on either mock-infected or HSV-infected neurons. ACV was not needed to maintain latency. The drug was removed 7 days after inoculation without any evidence of productive infection as determined by the absence of detectable infectious virus or cytopathic effect (CPE). It was found that with the use of AVC during the inoculation period, the MOI could be increased, within limits, without development of lytic infection. Consequently, both the survival of cultures and the percentage of cultures harboring HSV were increased to 100% (Table 1). FIG. 1 shows the time course of the expression of infectious HSV released into the culture medium at various times after the inoculation with 1 PFU of HSV per cell. The virus was rapidly absorbed or inactivated as indicated by the small fraction of the initial viral inoculum detected in supernantants removed from the cultures immediately following the absorption period. Thereafter, cultures were followed after the inoculation without detecting infectious virus or CPE. Latent cultures, deprived of NGF by adding anti-NGF serum to the cultures, resulted in 100% of the cultures developing CPE and producing infectious HSV (FIG. 1 and Table 1). Infectious virus was detected in the culture medium 48–72 h after the addition of anti-NGF serum (FIG. 1 and Table 1). Infecting with MOI of 20, even the presence of 500 uM ACV, a dose well above the reported concentration producting 50% inhibition, $ED_{50}$ of 0.01 uM, was unable to prevent the destruction of the cultures (Table 1).

TABLE 1

Effect of acyclovir concentration verses the MOI
of HSV on survival and the establishment of latency

| ACYCLOVIR | PFU/CELL | % SURVIVAL | % REACTIVATION | |
|---|---|---|---|---|
| | | | ANTI-NGF | NORMAL SERUM |
| 10 μM | 0.05 | 100 (36/36)[a] | 22 (4/18) | 0 (0/18) |
| " | 0.5 | 100 (36/36) | 100 (18/18) | 0 (0/18) |
| " | 5 | 0 (0/36) | — | — |
| 50 μM | 1 | 100 (72/72) | 100 (36/36) | 0 (0/36) |
| " | 5 | 100 (176/176) | 100 (36/36) | 0 (0/36) |
| " | 10 | 0 (0/8) | — | — |
| 500 μM | 10 | 75 (6/8) | 100 (3/3/) | 0 (0/3) |
| " | 20 | 0 (0/8) | — | — |

[a]Number of positive cultures/total number of cultures tested.

Neuronal cultures were treated with ACV at the concentrations indicated for 7 days following inoculation with HSV-1 (strain 115), thereafter the drug was removed from the culture medium.

The percentage of cultures surviving was determined 2 weeks post-inoculation. Viability was based on neuronal morphology and culture supernatants were tested in plaque-forming assays for infectious HSV.

The percent reactivation of cultures was determined two weeks post-inoculation. At this time surviving cultures were treated with either 1% guinea pig anti-NGF serum or 1% nonimmune guinea pig serum. Cultures were evaluated for CPE and cultures were harvested on day 5 after serum treatment to test for the presence of infectious virus by plaque-forming assays. Cultures were considered positive when both CPE and infectious virus were detected.

Latent cultures were deprived of NGF by several washings with medium lacking NGF. Under these conditions reactivation from 100% of the cultures (16 out of 16) was observed. There was a delay of approximately 24 h before virus was detected compared to results obtained using anti-NGF antibodies, consistent with the known difficulty in removing NGF, which nonspecifically binds to many substrates. These data demonstrate that the signal for reactivation was the removal of NGF and was not a nonspecific function of the antiserum.

EXAMPLE 3

IMMUNOHISTOCHEMICAL DETECTION OF HSV

Indirect immunohistochemistry was used to determine whether detectable levels of viral antigens were expressed during the latent phase of the infection. Neuronal cultures were inoculated with MOI of 1 of HSV-1 (115) in the presence of 50 uM ACV. ACV was removed from the cultures after 7 days. Fourteen days after viral inoculation, HSV-infected and mock-infected cultures were treated with anti-NGF or nonimmune serum. Twenty four h after the initiation of treatment, the cultures were fixed and processed as described in Example 1. Immunohistochemical staining was performed using a general anti-HSV serum or a monotypic antiICP4 serum as the primary antibodies.

In three experiments, 8 cultures in each, there was no positive immunostaining with either primary antibody during the latent phase of the infection in cultures treated with nonimmune serum. However, when latent cultures were treated with anti-NGF, immunoreactive staining using the polyclonal anti-HSV serum was evident on the neuronal soma within 12 h after the addition of anti-NGF. By 24 h after anti-NGF treatment, staining was extensive and present on both the neuronal cell bodies as well as the neurites. Immunoreactive staining was present only on neurons 24 h after anti-NGF treatment and essentially all of the neurons in the cultures had extensive staining.

EXAMPLE 4

SUPPRESSION OF VARIOUS STRAINS OF HSV BY NGF

Based on evidence that certain HSV strains are restricted in neurovirulence and that HSV types are neurotropic as to the site of latency (for example, HSV-1 tends to establish latency in ganglia above the waist, while HSV-2 generally established latent infections in ganglia below the waist) studies were done to determine whether the establishment of HSV latency was restricted in vitro by HSV strain or type.

Four additional strains of HSV-1 and one strain of HSV-2 were tested for their ability to establish latent infections and to reactivate in response to NGF deprivation. Under the conditions studied, HSV-2 (G) and 3 of the 4 strains of HSV-1 established latent infections and reactivation occurred in response to NGF deprivation (Table 2).

TABLE 2

Percentage of survival and establishment of latent
infections in neuronal cultures after infection with
herpes simplex viruses

| VIRUS | % SURVIVAL | % REACTIVATION | |
|---|---|---|---|
| | | ANTI-NGF | NORMAL SERUM |
| HSV-1, F | 100 (72/72)[a] | 100 (36/36) | 0 (0/36) |
| HSV-1, HRM | 100 (16/16) | 100 (8/8) | 0 (0/8) |
| HSV-1, KOS | 100 (16/16) | 100 (8/8) | 0 (0/8) |
| HSV-1, McINTYRE | 0 (0/16 | — | — |
| HSV-2, G | 100 (16/16) | 100 (12/12) | 0 (0/4) |

[a]Number of positive cultures/total number of cultures tested.

Neuronal cultures were infected with a MOI of 1 in the presence of 50 uM acyclovir. One week postinoculation, the acyclovir was removed from the cultures.

The percentage of cultures surviving were evaluated morphologically 2 weeks post-inoculation. Additionally, culture supernatants were tested for infectious virus in plaque-forming assays.

In determining the percentage of the cultures that reactivated the cultures were evaluated morpho-logically and the culture media was tested in plaque-forming assays. Cultures were considered positive for reactivation when the cultures had both CPE and detectable infectious virus.

This data indicates that the effect of NGF is not unique to a particular strain or type of HSV. HSV-1 (McIntyre) resulted in the lytic destruction of the cultures and was only syncycial-forming strain tested. This characteristic or increased neurovirulence may explain the observation.

EXAMPLE 5

SUPPRESSION OF HSV REACTIVATION BY NGF IN COMBINATION WITH VARIOUS VIRAL INHIBITORS

Several additional agents, which inhibit HSV DNA polymerase at unique sites (Honess, et al., *Journal of Virology*, 148, 1974), were tested for their effects on the establishment of latency. Cultures were treated for 12 h prior and for 7 days after inoculation with HSV, thereafter the drug was removed from the culture medium by several changes of medium. At the concentrations of aphidicolin and phosphonoacetic acid used, there was no apparent toxic effects and there was no apparent loss in the number of neurons. Treatment of the cultures with aphidicolin or phosphonoacetic acid resulted in the survival of 100% of the cultures and 100% of the cultures harbored latent virus (Table 3).

TABLE 3

Effects of viral DNA polymerase inhibitors on the percentage of cultures surviving and with latent virus following HSV inoculation

| | | | % REACTIVATION | |
|---|---|---|---|---|
| DRUG | CONC. | % SURVIVAL | ANTI-NGF | NORMAL SERUM |
| Aphidicolin | 10 μM | 100 (72/72)[a] | 100 (36/36) | 0 (0/36) |
| Phosphono-acetic acid | 100 μg/ml | 100 (24/24) | 100 (12/12) | 0 (0/12) |

[a]Number of positive cultures/total number of cultures tested.

Neuronal cultures were treated with the drug at the concentrations indicated for 7 days following inoculation with MOI of 1 of HSV-1 (strain 115), thereafter the drug was removed from the culture medium.

To determine percent survival, cultures were evaluated 2 weeks post-inoculation for viability based on neuronal morphology and culture supernatants were tested in plaque-forming assays for the presence of infectious HSV.

To determine percent reactivation, surviving cultures were treated two week postinoculation with either 1% guinea pig anti-NGF serum or 1% nonimmune guinea pig serum. Cultures were evaluated for CPE and were harvested on day 5 after serum treatment to test for the presence of infectious virus by using plaque-forming assays.

Reactivation was observed as the result of NGF deprivation; nonimmune serum did not produce reactivations. After the addition of anti-NGF, latent cultures developed CPE and released infectious virus following a similar time course as observed with ACV/treated cultures described above (not shown).

EXAMPLE 6

EFFECTS OF NGF DEPRIVATION ON LATENT HSV

Neuronal cultures were established as described in Example 1,B. After exposure of the cultures to 5-fluorodeoxyuridine for 10-12 days the drug was removed from the culture medium. The neuronal cultures were then inoculated with HSV at the multiplicity of infection (the number of infectious virus particles/cell) of HSV indicated in Table 4. After virus adsorption, the inoculum was removed and standard culture media containing 1% human anti-HSV serum was added. Antiserum to HSV, which enhanced survival of the cultures probably by limiting viral spread, was rinsed from the cultures after 10 days.

TABLE 4

Effects of MOI levels on survival of neuronal cultures and the frequency of HSV reactivation after NGF deprivation

| MOI[a] | % Survival[b] | % Reactivation |
|---|---|---|
| 0.03 | 100 (120/120) | 8 (5/60) |
| | 100 (120/120) | 10 (6/60) |
| 0.1 | 100 (52/52) | 19 (5/26) |
| 0.5 | 93 (119/128) | 26 (15/54) |
| | 94 (120/128) | 24 (15/63) |
| 0.1 | 63 (38/60) | 53 (10/19) |

[a]MOI, multiplicity of infection with HSV (plaque-forming units/cell). HSV, type 1, F strain, used for the inoculations, was prepared and titered on Vero cells.
[b]Number of positive cultures/number of cultures tested.

Cultures infected with multiplicities of infection of 0.03 and 0.1 retained normal morphology at all times observed. Those cultures inoculated with 0.5 and 1.0 pfu/cell, 6% and 37%, respectively, developed HSV-specific dytopathology and were lysed between 6-8 days postinoculation. Those neuronal cultures which retained normal morphology following HSV inoculation, had no evidence of viral infection (no infectious virus, no virus-encoded thymidine kinase activity, and no viral antigens detectable by immunohistochemistry) at any of the time tested (5 weeks post-inoculation was the longest time point examined). However, NGF deprivation (produced by adding antibodies to NGF to the culture medium) resulted in the production of infectious HSV, viral thymidine kinase activity, and viral antigens. Sister cultures that had also been infected with HSV, but were treated with non-immune serum, did not produce any active virus infection. These data indicate that the cultures harbored latent HSV since there was no detectable virus and reactivation of latent virus occurred with NGF deprivation as shown by the presence of detectable virus. The percentage of cultures resulting in reactivation was dependent on the multiplicity of infection used or inculation of 1.0 pfu/cell (Table 4). This is the first in vitro system for HSV latency in neurons that duplicates the phenomenon observed in humans.

EXAMPLE 7

EFFECTS OF NGF ON PRIMARY HSV INFECTION

Using the mouse model characterized by Price, et al. Nature (London), 257:686,1975), mice were inoculated with HSV, type 1 in the anterior eye chamber and treated daily with either 1 mg/kg NGF or normal saline, intraperitoneally. Table 5 shows the results of assays of the superior cervical ganglia for infectious virus on day 5 post-inoculation. Separate experiments have shown that day 5 post-inoculation was the peak time for virus replication in the ganglia.

TABLE 5

| Plaque-forming units of HSV in the homogenates of the superior cervical ganglion for mice on day 5 post-inoculation | |
|---|---|
| Saline-treated (n = 10) | NGF-treated (n = 10) |
| $16.2 \pm 5.7^a$ | $0^b$ |

The number in parenthesis are the number of ganglia assayed.
[a] Mean ± SEM.
[b] $P = 0.001$ This data shows that exogenous NGF prevents or significantly reduces HSV replication during the primary infection in the ganglia. These results in primary infections, in combination with the results in the in vitro model of latency, indicate physiological and pharmacological roles for NGF in controlling HSV that should be applicable to other viruses capable of infecting NGF-responsive neurons.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A method for ameliorating viral disease in an animal, wherein said animal has neural cells infected with latent or active Herpes Simplex Virus Type 1 or Type 2, which method comprises administering to said animal a therapeutically effective amount of purified mammalian-derived nerve growth factor.

2. The method of claim 1, wherein said nerve growth factor is administered in conjunction with a therapeutically-effective amount of a Herpes Simplex Virus antiviral agent, wherein the dose of said nerve growth factor is in a range of from about 0.01 to about 10 mg per kg of body weight per day.

3. The method of claim 2, wherein said antiviral agent inhibits viral DNA polymerase.

4. The method of claim 3, wherein said antiviral agent is acyclovir or phosphonoacetic acid.

5. A pharmaceutical composition for ameliorating viral disease in an animal having neural cells infected with latent or active Herpes Simplex Virus comprising purified mammalian-derived nerve growth factor and a therapeutically-effective amount of a Herpes Simplex Virus antiviral agent, said nerve growth factor being in a range of from about 0.01 to about 10 mg per kg of body weight per day.

6. The composition of claim 5, wherein said antiviral agent is a viral DNA polymerase inhibitor.

7. The composition of claim 6, wherein said antiviral agent is acyclovir or phosphonoacetic acid.

8. The composition of claim 5, wherein said Herpes Simplex Virus is HSV-1 or HSV-2.

9. The compositions of claim 7 wherein said antiviral agent is acyclovir.

10. The composition of claim 9 wherein the composition comprises from about 15 to about 30 mg per kilogram of body weight per day of said acyclovir.

* * * * *

UNITED STATES PATENT AND TRADEMARK OFFICE
CERTIFICATE OF CORRECTION

PATENT NO. : 5,232,695
DATED : August 3, 1993
INVENTOR(S) : Wilcox, et al.

It is certified that error appears in the above-indentified patent and that said Letters Patent is hereby corrected as shown below:

Column 2, line 51, reading "serum O did" should read -- serum (O) did --.

Column 5, line 27, reading "969)," should read -- 1969), --.

Column 5, line 32, reading "did not effect" should read -- did not affect --.

Column 8, line 59, reading "0(0/16" should read -- 0(0/16) --.

Signed and Sealed this

Fifteenth Day of November, 1994

Attest:

BRUCE LEHMAN

Attesting Officer          Commissioner of Patents and Trademarks